May 8, 1973 F. W. ANDERSON Plant Pat. 3,328
NECTARINE TREE
Filed Sept. 30, 1971
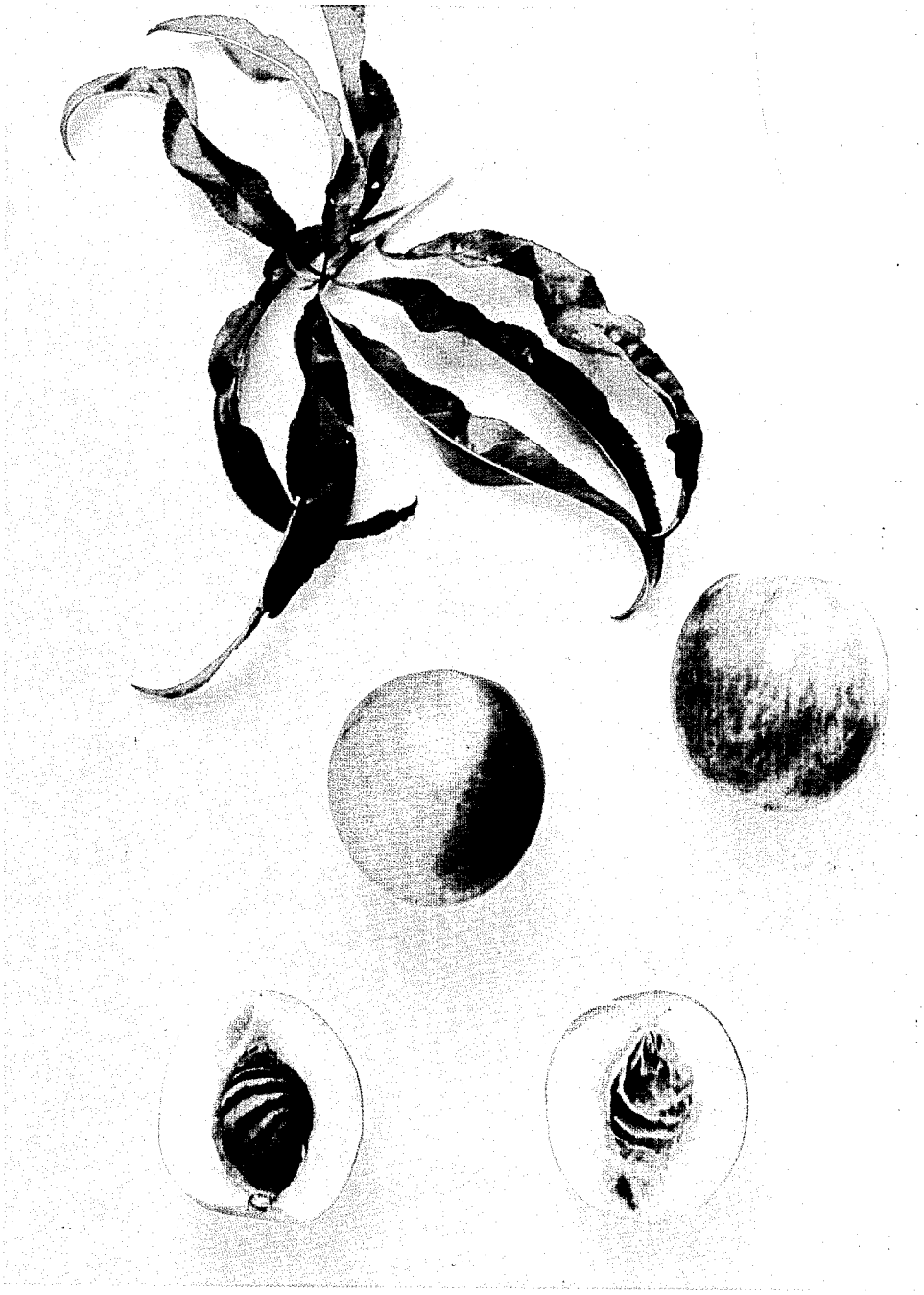

United States Patent Office

Plant Pat. 3,328
Patented May 8, 1973

3,328

NECTARINE TREE

Frederic W. Anderson, Merced, Calif., assignor to Reedley Nursery, Inc., Reedley, Calif.

Filed Sept. 30, 1971, Ser. No. 185,456
Int. Cl. A01h 5/03
U.S. Cl. Plt.—41 1 Claim

ABSTRACT OF THE DISCLOSURE

A nectarine tree, of medium size, which is vigorous, spreading, open, and very productive of large to medium size, globose to oblong, uniform, symmetrical, freestone fruit having yellow skin completely overspread with red at maturity, and yellow flesh with red at the surface of the pit cavity streaked into the flesh; the fruit being slightly larger, having a brighter red exterior color, and ripening about ten days later, than the fruit of the Sun Grand nectarine (United States Plant Patent No. 974).

BACKGROUND OF THE VARIETY

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

ORIGIN OF THE VARIETY

The present variety of nectarine tree was originated by me, in my experimental nursery and orchard, located as aforesaid, as an $F_1$ cross between the Red Grand nectarine (United States Plant Patent No. 1,060) and the Early Sun Grand nectarine (United States Plant Patent No. 1,420). Seedlings resulting from such cross were maintained by me under careful and continuing observation, and, in maturity, one such seedling—and which is the present variety—evidenced certain novel characteristics. I, therefore, selected such one seedling for asexual reproduction in anticipation of ultimate commercial growing of the variety.

ASEXUAL REPRODUCTION OF THE VARIETY

Subsequent to origination and selection by me of the present variety of nectarine tree, in the manner above described, I asexually reproduced it by top-working on mature nectarine trees in my said experimental orchard, and—in maturity—such reproductions ran true to the original tree in all respects.

SUMMARY OF THE VARIETY

The herein claimed variety of nectarine tree is, characteristically, of medium size, vigorous, spreading, open, and very productive of large to medium size, globose to oblong, uniform, symmetrical, freestone fruit having yellow skin completely overspread with red at maturity, and yellow flesh with red at the surface of the pit cavity streaked into the flesh; such fruit, in comparison to the fruit of the Sun Grand nectarine, being slightly larger, having a brighter red exterior color, and ripening about ten days later, thus extending the shipping period for this type of nectarine.

BRIEF DESCRIPTION OF THE DRAWING

The drawing is an illustration, by photographic reproduction in color, of leaves and fruit of the present variety; one fruit being cut into halves, with the stone remaining in one half.

DESCRIPTION OF THE VARIETY

The botanical details of this new and distinct variety of nectarine tree—with color definitions (except those in common color terms) referenced to Maerz and Paul Dictionary of Color—are as follows:

Tree:
- *Size.*—Medium.
- *Vigor.*—Vigorous.
- *Growth.*—Spreading.
- *Density.*—Open.
- *Production.*—Very productive.

Trunk:
- *Size.*—Medium.
- *Texture.*—Medium.

Branches:
- *Size.*—Medium.
- *Texture.*—Smooth.

Leaves:
- *Size.*—Medium to small, average length—6¼", average width—¾".
- *Form.*—Lanceloate, acutely pointed.
- *Thickness.*—Thin.
- *Texture.*—Rugose.
- *Margin.*—Crenate.
- *Petiole.*—Medium length, medium thickness.
- *Glands.*—Average number—4, alternate, medium size, reniform, position—usually 2 on blade and 2 on petiole.
- *Color.*—Top side—medium green (22–L–8), under size—lighter green (21–I–7).

Flower buds:
- *Size.*—Medium.

Flowers:
- *Blooming period.*—Medium, as compared with other varieties—about with July Elberta peach (United States Plant Patent No. 15).
- *Size.*—Large showy.

Fruit:
- *Maturity when described.*—Eating ripe—Aug. 10, 1971.
- *Date of first picking.*—Aug. 1, 1971.
- *Date of last picking.*—Aug. 10, 1971.
- *Size.*—Uniform, large to medium average diameter axially—2⅜", average transversely in suture plane—2 5/16".
- *Form.*—Uniform, symmetrical, globose to oblong.
- *Suture.*—Distinct, extends from base to beyond apex.
- *Cavity.*—Rounded, circular.
- *Apex.*—Short, depressed.
- *Pistill point.*—Extremely small.

Skin:
- *Thickness.*—Medium.
- *Texture.*—Medium.
- *Tendency to crack.*—None.
- *Down.*—Wanting.
- *Color.*—Yellow (10–J–6) completely overspread, at maturity, with red (5–L–8) shading darker to India red (7–L–6).

Flesh:
- *Texture.*—Firm, meaty.
- *Fibers.*—Few.
- *Ripens.*—Evenly.
- *Flavor.*—Delicate, vinous.
- *Eating quality.*—Good to best.
- *Color.*—Yellow (10–K–7). Surface of pit cavity—Red (7–J–6), with the red streaked into the flesh.

Stone:
- *Type.*—Free.
- *Size.*—Medium, average length—1⅜", average breadth—1⅛", average thickness—1".

*Form.*—Oblong.
*Base.*—Oblique.
*Apex.*—Acute.
*Sides.*—Equal.
*Tendency to split.*—Very slight.
*Color.*—Brown (8–L–10).

Use: Market—local and long distance shipping.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, of medium size, vigorous, spreading, open, and very productive of large to medium size, globose to oblong, uniform, symmetrical, free stone fruit having yellow skin completely overspread with red at maturity, and yellow flesh with red at the surface of the pit cavity streaked into the flesh; such fruit, in comparison to the fruit of the Sun Grand nectarine, being slightly larger, having a brighter red exterior color, and ripening about ten days later.

No references cited.

ROBERT E. BAGWILL, Primary Examiner